US012607545B2

(12) United States Patent
Hunger et al.

(10) Patent No.: US 12,607,545 B2
(45) Date of Patent: Apr. 21, 2026

(54) DRILLING NEEDLE, DRILLING RESISTANCE MEASURING DEVICE AND USE THEREOF FOR INVESTIGATING PROPERTIES OF WOOD

(71) Applicant: IML Instrumenta Mechanik Labor GmbH, Wiesloch (DE)

(72) Inventors: Erich Hunger, Karlsruhe (DE); Sebastian Hunger, Leimen (DE); Fabian Hunger, Leimen (DE)

(73) Assignee: IML Instrumenta Mechanik Labor GmbH, Wiesloch (DE)

( * ) Notice: Subject to any disclaimer, the term of this patent is extended or adjusted under 35 U.S.C. 154(b) by 392 days.

(21) Appl. No.: 18/566,025

(22) PCT Filed: Jun. 2, 2022

(86) PCT No.: PCT/EP2022/065108
§ 371 (c)(1),
(2) Date: Nov. 30, 2023

(87) PCT Pub. No.: WO2022/253976
PCT Pub. Date: Dec. 8, 2022

(65) Prior Publication Data
US 2024/0361221 A1 Oct. 31, 2024

(30) Foreign Application Priority Data
Jun. 4, 2021 (DE) ...................... 20 2021 103 038.0

(51) Int. Cl.
*G01N 3/56* (2006.01)
*B27G 15/00* (2006.01)
(Continued)

(52) U.S. Cl.
CPC ............... *G01N 3/56* (2013.01); *B27G 15/00* (2013.01); *G01N 3/40* (2013.01); *G01N 33/46* (2013.01); *G01N 2203/0053* (2013.01)

(58) Field of Classification Search
CPC ........... G01N 3/56; G01N 3/40; G01N 33/46; G01N 2203/0053; B27G 15/00
See application file for complete search history.

(56) References Cited

U.S. PATENT DOCUMENTS

| | | | | |
|---|---|---|---|---|
| 4,480,952 A | * | 11/1984 | Jeremias | ................. B23B 51/00 408/1 R |
| 6,629,805 B1 | * | 10/2003 | Eischeid | ........... B23B 51/00035 408/230 |

(Continued)

FOREIGN PATENT DOCUMENTS

| | | |
|---|---|---|
| DE | 4122494 A1 | 3/1992 |
| DE | 4438383 A1 | 5/1996 |

(Continued)

*Primary Examiner* — Ryan J. Walters
(74) *Attorney, Agent, or Firm* — Smartpat PLC

(57) ABSTRACT

A drilling needle includes a needle head at one end of a needle shank. The needle head has a flattened wedge portion with two wedge faces and a cutter portion with two cutting faces, which each adjoin one of the wedge faces and adjoin one another at a top edge that runs at a right angle to an axis of rotation. The needle head has on each side a relief face, which forms a cutting edge with each of the cutting faces. The cutting edge forms, with the respective other one of the cutting faces, a secondary edge that trails with respect to the direction of rotation. A relief angle, spanned by a virtual straight line through the cutting edge corner and a secondary edge and a plane that extends perpendicular to the top edge in the axis of rotation, lies in a range from 6° to 10°.

10 Claims, 5 Drawing Sheets

(51) Int. Cl.
G01N 3/40 (2006.01)
G01N 33/46 (2006.01)

(56) References Cited

U.S. PATENT DOCUMENTS 7,267,513 B2 * 9/2007 Wiker ................... B27G 15/00
408/214
2006/0083595 A1 4/2006 Wiker et al.

FOREIGN PATENT DOCUMENTS

| | | | |
|---|---|---|---|
| DE | 10031395 | A1 | 4/2001 |
| DE | 102009013069 | A1 | 2/2010 |
| DE | 102013001711 | A1 | 8/2014 |
| JP | 2002039929 | A | 2/2002 |
| WO | 9805459 | A1 | 2/1998 |

* cited by examiner

DRILLING NEEDLE, DRILLING RESISTANCE MEASURING DEVICE AND USE THEREOF FOR INVESTIGATING PROPERTIES OF WOOD

CROSS-REFERENCE TO RELATED APPLICATION

This application is a national stage application, filed under 35 U.S.C. § 371, of International Patent Application PCT/EP2022/065108, filed on Jun. 2, 2022, which claims the benefit of German Patent Application DE 20 2021 103 038.0, filed on Jun. 4, 2021.

TECHNICAL FIELD

The disclosure relates to a drilling needle and a drilling resistance measuring device with such a drilling needle, along with its use for examining properties of wooden objects.

BACKGROUND

It is known from the prior art to examine tree trunks and wooden poles—i.e., living and dead wooden objects—for possible defects such as rot or the like. In any case, a minimally invasive examination is desirable since no harm should be caused by the examination. Drilling resistance measuring devices are used for these examinations. Such a drilling resistance measuring device is known, for example, from DE 10 2013 001 711 A1. In such drilling resistance measuring devices, thin drilling needles are used for the monitored drilling resistance measurement process. The drilling needle is rotated at high speed and advanced axially, wherein the power consumption of the needle drive is a measure of the penetration or drilling resistance, as the case may be, such that a drilling resistance profile can be recorded over the axial advance path of the drilling needle.

It is known to guide such drilling needles in a centered manner during the drilling process, i.e., to support them against a movement transverse to the drilling direction. For example, a special bucket telescope is known from DE 100 31 395 A1, which guides the drilling needle into passage openings at the bottom of the buckets and can be retracted by moving the smaller buckets into the next larger one. The drilling needle, which usually consists of a long shank with a drilling needle head at the end that has a drilling point or cutting edge, is not described in detail.

A device for testing wood is also known from DE 41 22 494 B4. This device also has cylindrical telescopic sleeves in which the drilling needle is guided centrally. The head of the drilling needle shown is flattened with a widened drilling tip, such that the diameter of rotation of the drilling needle head is larger than the shank diameter.

A needle that also shows a wider head than shank can also be seen in DE 44 38 383 C2: The needle shank merges into a wide cutting edge with a pointed spike.

The needle head of the drilling needle from DE 10 2009 013 069 A1 is intended to provide uniform rotation of the needle and to displace the cut wood material in the direction of the needle shank. For this purpose, the needle head also has a wide cutting edge at the end of a flattened wedge portion, the diameter of rotation of which is larger than the shank diameter, wherein the cutting edge runs at a right angle to the axis of rotation of the drilling needle. Thereby, the angle that the wedge portion spans to a plane, which is defined by the axis of rotation and the edge, is smaller than the angle that the cutting faces of the cutting edge span to the plane.

The known drilling needles are particularly suitable for a penetration angle horizontally and at a right angle to the object axis. However, since rot in wooden poles whose base section is in the ground is usually located about 10 cm below ground level, it is essential to drill holes at an angle of 15° to 45° to ground level for inspecting the poles, in order to be able to reach rot areas with the drilling needle without excavating the base of the pole. Thereby, ground level refers to a virtual average plane of the ground surface in the standing area of the wooden object. Conventional drilling needles tend to drift when penetration angles deviate from 90° to the object axis, wherein the needle deviates from the intended axial feed direction, such that a straight-line drilling channel is not created; rather, a channel that can even miss the rot area is created.

SUMMARY

The present disclosure shows how to improve a drilling needle in such a manner that the insertion of the drilling needle into the object is reliably carried out at an angle deviating from 90° to the object axis, in particular in order to be able to examine object sections below ground level.

This is achieved by a drilling needle as disclosed herein and by a drilling resistance measuring device as disclosed herein. A use of the drilling needle or the drilling resistance measuring device, as the case may be, for examining properties of wood is disclosed.

A first embodiment of the drilling needle relates to a drilling needle having a drilling needle head, which has, at one end of a drilling needle shank, a flattened wedge portion having two diametrical wedge faces and a cutter portion having two cutting faces, which each adjoin one of the wedge faces and adjoin one another at a top edge that runs at a right angle to an axis of rotation A of the drilling needle shank. Furthermore, the wedge portion has two diametrical flank segments that adjoin on the side the wedge faces and are rounded. The head of the drilling needle has a relief face on the side adjoining each of the two cutting faces, the design of which is matched to a direction of rotation of the drilling needle. Thus, each of the two relief faces forms, with one of the cutting faces in each case, a cutting edge that leads with respect to the direction of rotation and extends from a top corner at the top edge to a cutting edge corner at the wedge face. Accordingly, each of the two relief faces forms with the other of the cutting faces a secondary edge that trails with respect to the direction of rotation, extending from the respective top corner at the top edge to a secondary edge corner at the wedge face. Thereby, a relief angle α, which a virtual straight line that runs through the cutting edge corner and the secondary edge corner spans with a plane that extends through the axis of rotation A perpendicular to the top edge, lies in a range from 6° to 10°. This means that the trailing secondary edge is shorter than the leading cutting edge. Therefore, the relief face has the shape of an irregular quadrilateral with one side rounded due to the rounded flank segment, wherein the four corners are the top corner, cutting edge corner, secondary edge corner and another corner adjacent to the secondary edge corner at the edge between the wedge face and flank segment.

According to a further embodiment of the drilling needle, the relief angle α can be 8°.

When using the drilling needle with the specific drilling needle head geometry, the drifting or non-straight running, as the case may be, of the drilling needle during penetration, in particular at a penetration angle deviating from 90° to the object axis, is minimized, since the cutting edge with the undercut relief face prevents the drilling needle from touching the annual rings first with the top edge upon penetration deviating from 90° to the object axis. Thus, the drilling needle reliably enables straight-line drilling, in particular at an angle of 15° to 45° to ground level as well.

According to a further embodiment of the drilling needle, a cutting edge angle γ, which the cutting edge spans with respect to the axis of rotation or with respect to a plane perpendicular to the top edge through the axis of rotation, can lie in a range of 25° to 35°, preferably it is 30°.

Further embodiments of the drilling needle can provide that the top edge has a width that provides a first diameter of rotation that is wider than a diameter of the drilling needle shank, such that chips can be displaced in the direction of the shank. Preferably, the drilling needle head thereby can also have a second diameter of rotation in a transition region of the wedge portion with the cutter portion, i.e. in the region of the rounded side of the relief face on the flank segment, which is larger than the first diameter of rotation, since the relief face ensures chip removal. Alternatively or additionally, for uniform rotation of the drilling needle, an angle δ between the two wedge faces can be smaller than a top edge angle β between the two cutting faces.

Thereby, the top edge angle β can lie in a range of 85° to 95° and preferably 90°, while the angle δ between the two wedge faces can lie in a range of 10° to 20° and can for example be 15°.

According to a further embodiment of a drilling needle, it can be provided that the drilling needle head or the entire drilling needle is made of a steel that can be surface-hardened or through-hardened, wherein at least the drilling needle head, preferably the entire drilling needle, has a surface coating.

According to a further embodiment of a drilling needle, a suitable surface coating can be formed by a hard chromium plating, alternatively the coating can comprise nickel or polytetrafluoroethylene; the coating can advantageously have a layer thickness in a range of 8 to 12 μm. Alternatively, the drilling needle, at least its cutting end, can also be hardened by nitriding.

According to an exemplary embodiment of a drilling needle, a width of the top edge can lie in a range of 2.00 to 2.50 mm and is preferably 2.20 mm. Thereby, the drilling needle head has a maximum width in a transition region of the wedge portion with the cutter portion in the region of the rounding of the relief face between the cutting edge corner and the secondary edge corner, wherein such maximum width of the drilling needle head can lie in a range of 2.25 to 3.00 mm and is preferably 2.75 mm. The height of the cutter portion associated with this exemplary embodiment, which is defined by the axial distance from the top edge to the wedge portion edge extending between the cutting face and the wedge face from cutting edge corner to secondary edge corner, can be in the range of 0.30 to 0.40 mm, and is preferably 0.35 mm.

In general, all wooden materials can be worked on with the same needle; for particularly hard woods, it is advantageous to use a drilling needle with a hardened cutting edge.

In a first embodiment, a drilling resistance measuring device has a drilling needle and a hand-held device comprising at least one drive device with a drill chuck, in which the drilling needle as disclosed herein, is clamped. Further embodiments of the drilling resistance measuring device relate to the fact that the hand-held device can have a guide device for the guided insertion of the drilling needle into a wooden object to be examined and/or a drilling resistance detection device.

A use of a drilling resistance measuring device with a drilling needle for examining properties of a wooden object such as a pole or tree trunk provides that, when the drilling needle is inserted into the wooden object in an axial feed direction, which can be selected as desired with respect to an object axis or a ground level, a straight-line drilling channel is created in the axial feed direction. Preferably, the wooden object can have a portion below ground level and the drilling channel can extend from a penetration point above ground level into the portion below ground level, wherein a penetration angle ε between the axial feed direction and the ground level can lie in a range of 15° to 45°.

When using a drilling needle, portions of the wooden objects below ground level in particular can be examined, which require a penetration angle of 15° to 45° for a drilling point above ground level, wherein, unlike with conventional drilling needles, an exact straight-line drilling channel is created with the drilling needle.

Other embodiments, along with some of the advantages associated with these and other embodiments, will become clear and more readily understood from the following detailed description with reference to the accompanying figures. Items or parts thereof that are substantially the same or similar can have the same reference signs. The figures are merely a schematic representation of one embodiment of the invention.

DETAILED DESCRIPTION

Figure 3:
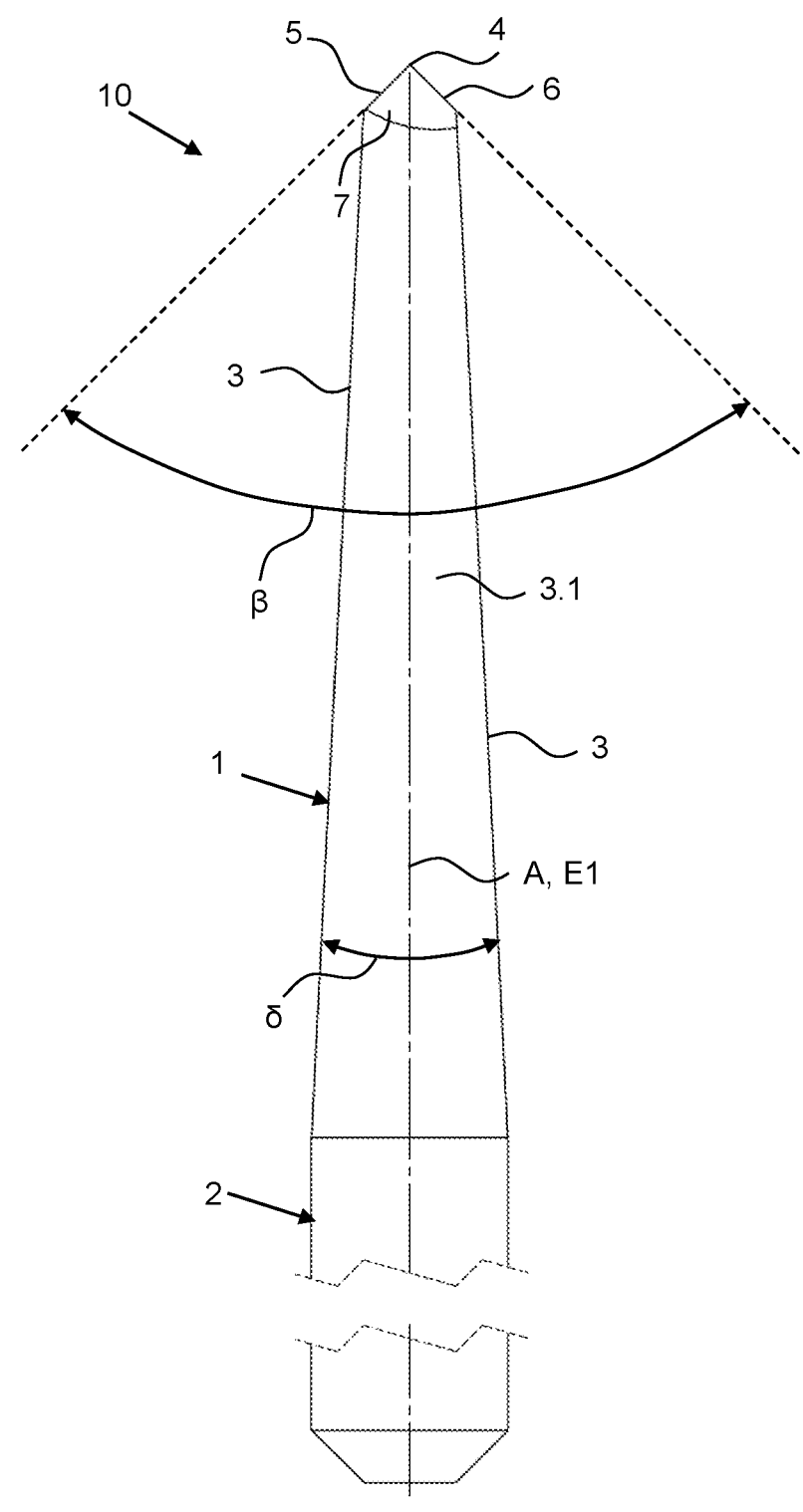
FIG. 3 is a first side view of the drilling needle of FIG. 1.
Figure 4:
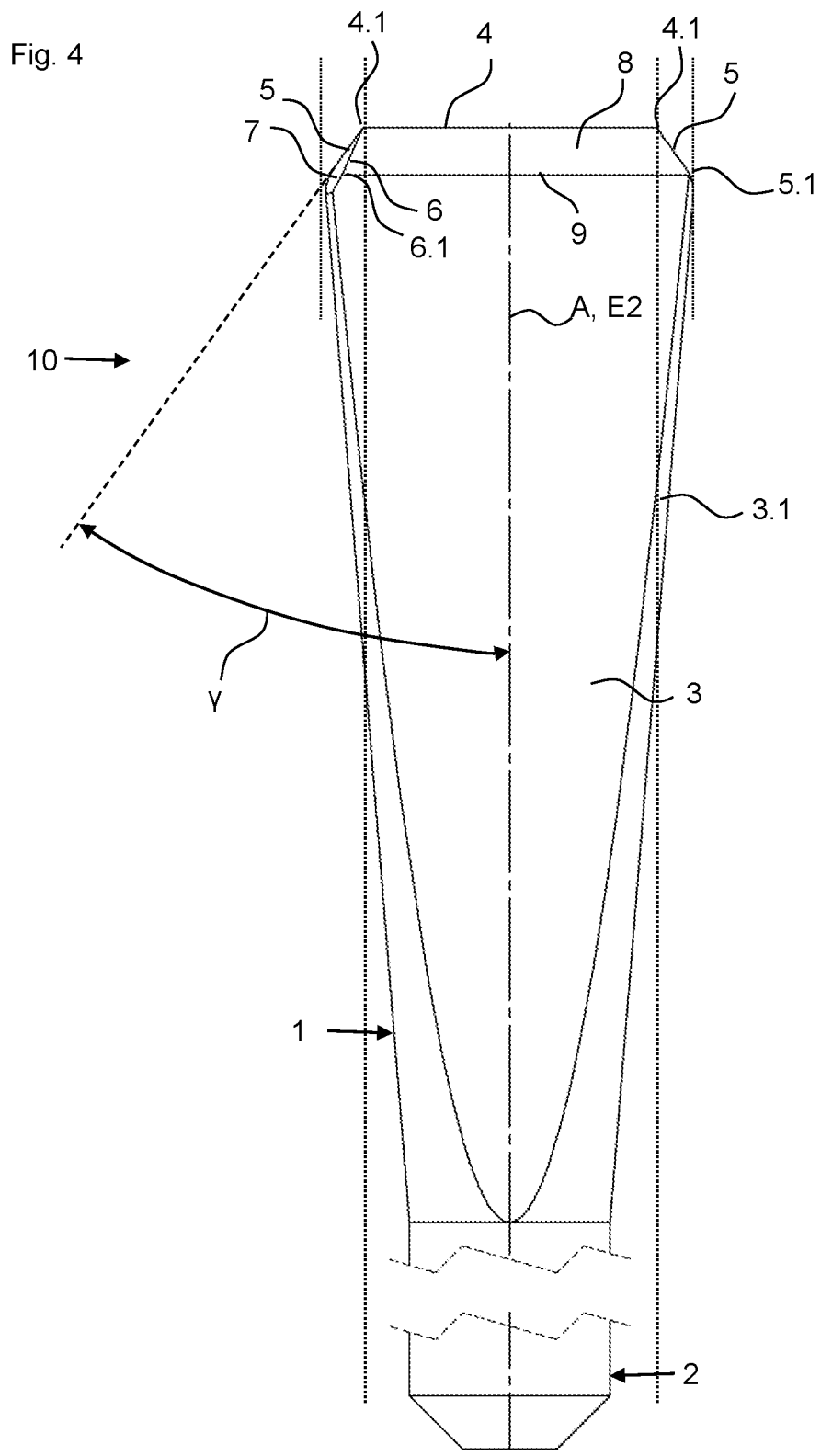
FIG. 4 is a second side view of the drilling needle of FIG. 1.
Figure 5:
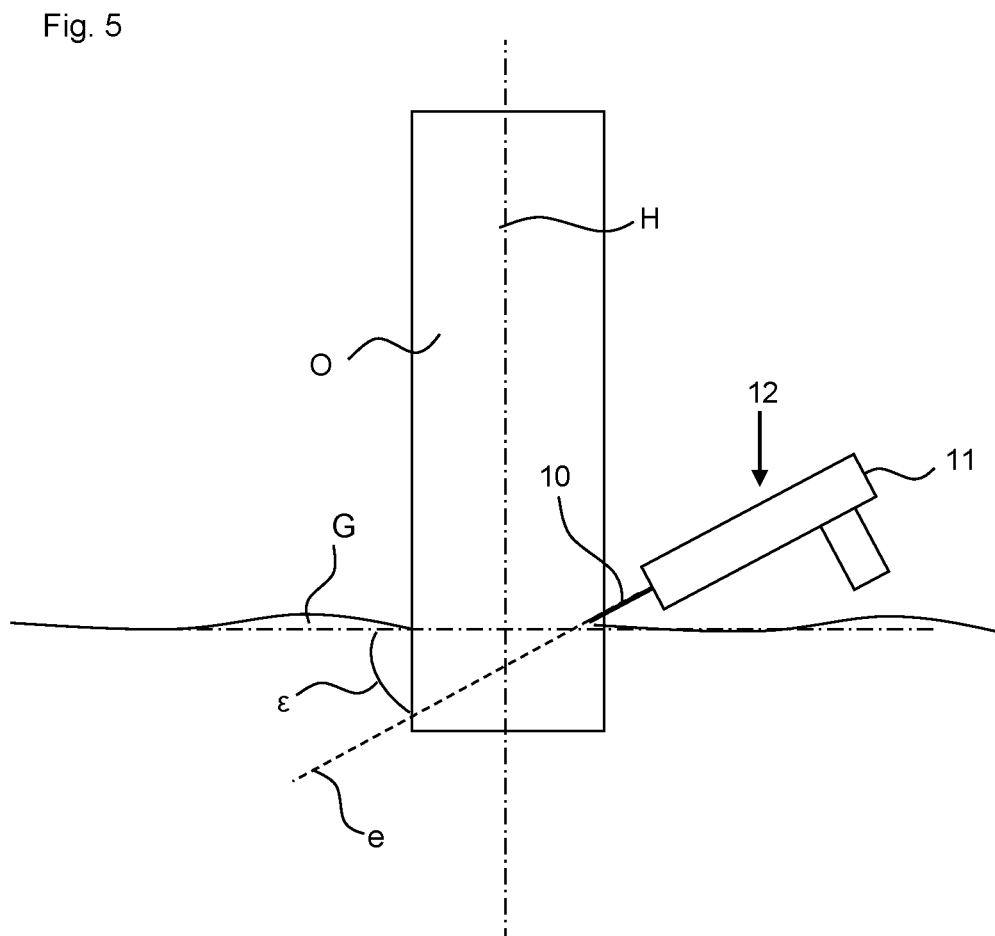
FIG. 5 is a schematic view of a wooden object to be examined with a drilling resistance measuring device.

FIGS. 1 to 4 show an example of a drilling needle 10 with a specifically shaped drilling needle head 1, which is particularly suitable for drilling resistance measurements by means of a drilling resistance measuring device 12, as indicated in FIG. 5, in a wooden object O at a penetration angle ε deviating from 90° with respect to the object axis H. A drilling resistance measuring device 12 uses a drilling needle 10 for examining properties of wooden objects O.

The specific shape of the drilling needle head 1 of a drilling needle 10, as shown in FIGS. 1 to 4, is based on a flattened wedge portion K followed by a cutter portion S at one end of the cylindrical drilling needle shank 2. The wedge portion K is defined by two wedge faces 3 lying in opposite directions, which are supplemented on the side by two corresponding rounded flank segments 3.1. The cutter portion S consists of two cutting faces 8 adjoining a top edge 4, which adjoin the wedge faces 3 and form a wedge portion edge 9 with each of them. The top edge 4 runs at a right angle to an axis of rotation A of the drilling needle shank 2, and allows the definition of a first reference plane E1 defined by the top edge 4 and the axis of rotation A. A second reference plane E2 runs perpendicular, i.e. at a right angle, to the top edge 4 and also through the axis of rotation A.

5

Figure 1:
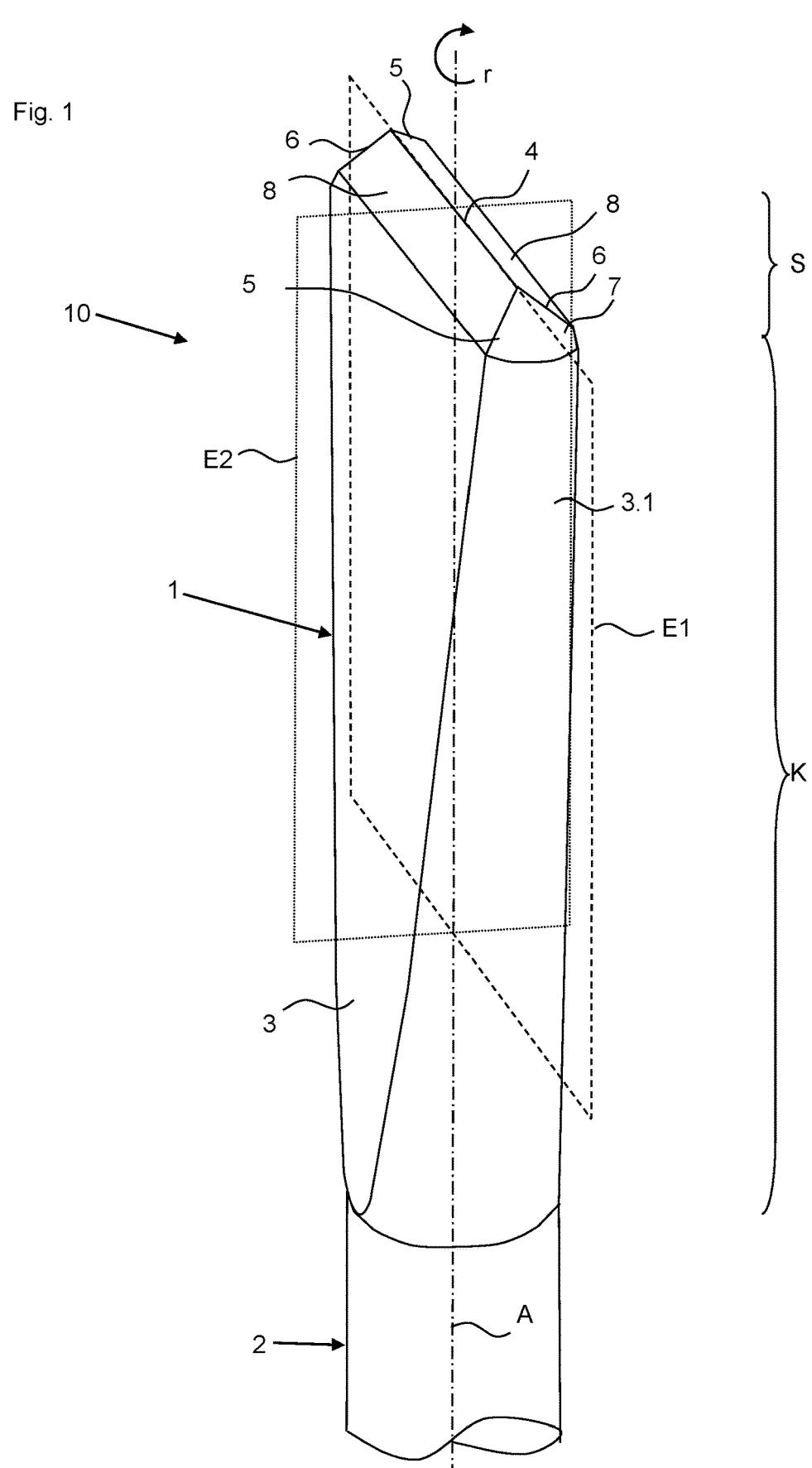
FIG. 1 is a perspective view of the drilling needle head of a drilling needle.
Figure 2:
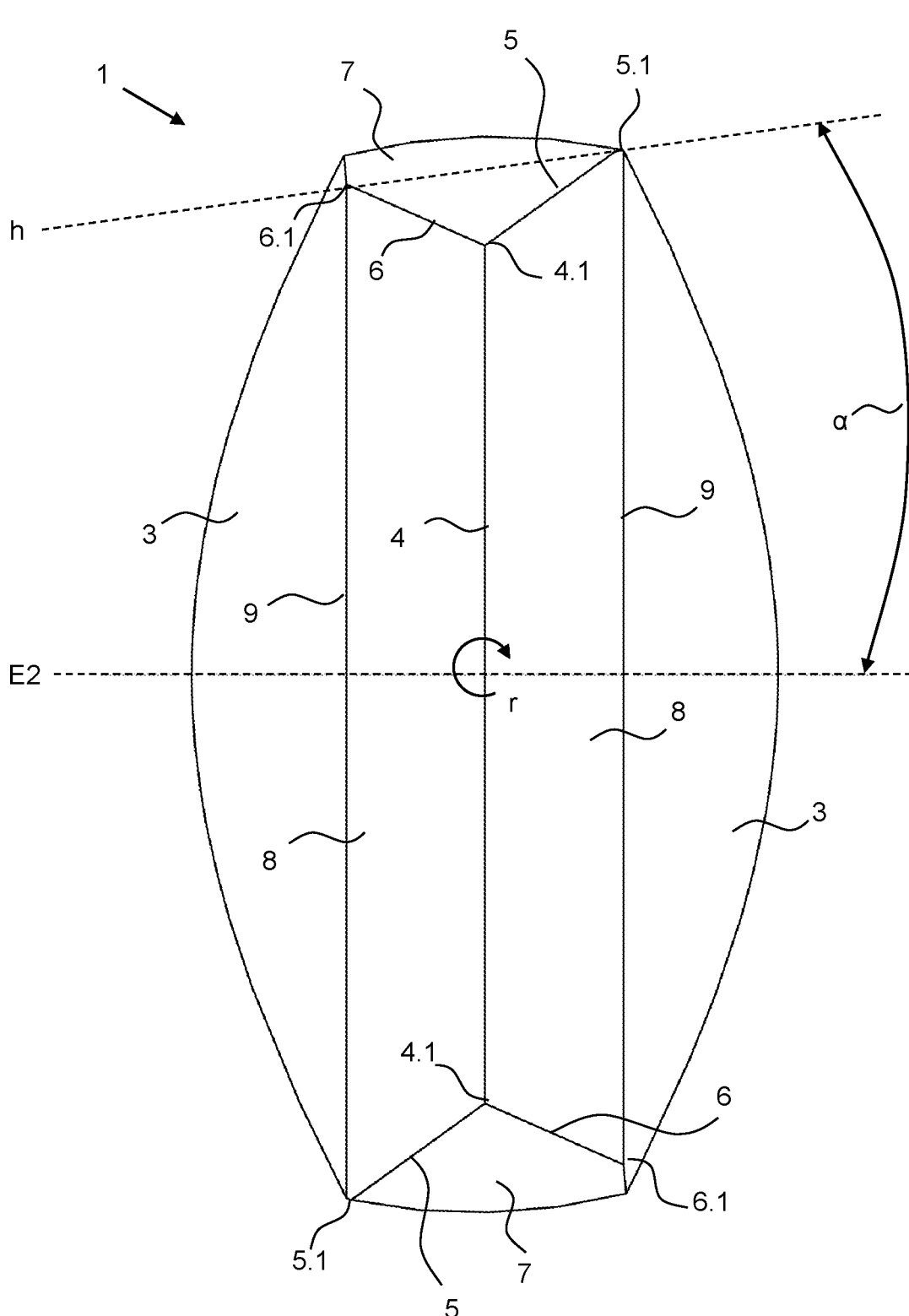
FIG. 2 is a top view of the drilling needle head from FIG. 1.

In the cutter portion S, the drilling needle head 1 has a relief face 7 on the side adjoining each of the two cutting faces 8, which—as can be seen particularly well in the plan view in FIG. 2—forms with one of the cutting faces 8 in each case a cutting edge 5 that leads with respect to a cutting edge 5 in direction of rotation r, which extends from a top corner 4.1 at the top edge 4 to a cutting edge corner 5.1 at the wedge face 3. With the respective other of the cutting faces 8, each relief face 7 forms a secondary edge 6 that trails with respect to the direction of rotation r, which extends from the top corner 4.1 on the top edge 4 to a secondary edge corner 6.1 on the wedge face 3. Both the two cutting edges 5 along with the two secondary edges 6 and the relief faces 7 bounded by them can be mapped into one another by rotation by 180° about the axis of rotation A and thus, in plan view, are point-symmetrical with respect to the axis of rotation. The relief angle α, which the virtual straight line h that runs through the cutting edge corner 5.1 and the secondary edge corner 6.1 spans with the plane E2 extending through the axis of rotation A perpendicular to the top edge 4, is 8° in the example shown and can lie in a range of 6° to 10°. Thus, the trailing secondary edge 6 is shorter than the leading cutting edge 5, such that the relief face 7 has the shape of an irregular quadrilateral with a rounded side that corresponds to the edge to the rounded flank segment 3.1. In addition to the top corner 4.1, the cutting edge corner 5.1 and the secondary edge corner 6.1, the relief face 7 has a further corner (not designated), which is present adjacent to the secondary edge corner 6.1 at the edge between the wedge face 3 and the flank segment 3.1.

FIG. 4 shows the cutting edge angle γ of a drilling needle 10 in an exemplary embodiment. The cutting edge angle γ is defined between the cutting edge 5 and the axis of rotation A or the plane E2 and is 30° in the example shown, but, in deviation from this, can lie in a range of 25° to 35°. Furthermore, it can be seen in FIG. 4 that, by the dotted lines, the top edge 4 provides a diameter of rotation that is wider than a diameter of the drilling needle shank 2, but is smaller than the diameter of rotation that the drilling needle head 1 has in the transition region of the wedge portion K with the cutter portion S, i.e., in the region of the rounded edge of the relief face 7 to the flank segment 3.1.

In the example shown in FIGS. 1 to 4, the top edge 4 has a width of 2.20 mm, while the maximum width of the drilling needle head 1 in the region of the rounded edge of the relief face 7 to the flank segment 3.1 at the transition region of the wedge portion K with the cutter portion S is 2.75 mm. Here, the height of the cutter portion S in the axial direction between the top edge 4 and the wedge portion edge 9 is 0.35 mm.

In deviation from these preferred dimensions, a drilling needle 10 can have a width of the top edge 4 in a range of 2.00 to 2.50 mm, wherein the maximum width of the drilling needle head 1 in the region of the rounded edge of the relief face 7 to the flank segment 3.1 can lie in a range of 2.25 to 3.00 mm, under the condition that the width of the top edge 4 is smaller than the maximum width. The height of the cutter portion S can lie in a range of 0.30 to 0.40 mm.

In the side view shown in FIG. 3, the angle δ between the two wedge faces 3 and the top edge angle β between the two cutting faces 8 are shown, wherein it can be seen that the angle δ between the two wedge faces 3, which here at 15° lies within the range from 10° to 20°, is significantly smaller than the top edge angle β, which in the example shown is 90°, but can in principle lie in a range from 85° to 95°.

According to a preferred embodiment, the drilling needle 10 can be made of a steel and have a hard chrome plating as a surface coating with a layer thickness in a range from 8 to 12 μm.

In FIG. 5, a drilling resistance measuring device 12 and its use for examining properties of a wooden object O are indicated. The drilling resistance measuring device 12 has a drilling needle 10, for example the drilling needle 10 shown in FIGS. 1 to 4, and a hand-held device 11, details of which are not shown and designated, but which has at least one drive device with a drill chuck in which the drilling needle 10 is clamped, and optionally a guide device for guided insertion of the drilling needle 10 into the wooden object O to be examined and/or a drilling resistance detection device.

Such drilling resistance measuring device 12, which has a drilling needle 10, can be used for examining properties of a wooden object O, wherein when the drilling needle 10 is inserted into the wooden object O in an axial feed direction e, which can be selected as desired with respect to an object axis H or a ground level G, a straight-line drilling channel is produced in the axial feed direction e by preventing drifting of the drilling needle 10 due to the specific design of the drilling needle head 1. Preferably, the wooden object O can have a portion below ground level G that is to be examined by the drilling resistance measuring device 12. For this purpose, the drilling channel can extend from a penetration point above the ground level G into the portion below the ground level G, in that a penetration angle ε between the axial feed direction e and the ground level G can be in a range from 15° to 45°. The penetration angle ε to reach a region of the object O to be examined below ground level G depends not only on the height of the penetration point into the object O above ground level G, but also on the diameter of the object O to be examined.

LIST OF REFERENCE SIGNS

1 Drilling needle head
2 Shank
3 Wedge face
3.1 Flank segment
4 Top edge
4.1 Top corner
5 Cutting edge
5.1 Cutting edge corner
6 Secondary edge
6.1 Secondary edge
7 Relief face
8 Cutting face
9 Wedge portion edge
10 Drilling needle
11 Hand-held device
12 Drilling resistance measuring device
A Axis of rotation
E1 Plane through axis of rotation and through top edge
E2 Plane through axis of rotation and perpendicular to top edge
G Ground level
H Object axis
K Flattened wedge portion
O Wooden object
S Cutter portion
e Feed direction
h Virtual straight line
r Direction of rotation
α Relief angle
β Top edge angle γ Cutting edge angle
δ Wedge face angle
ε Penetration angle

The invention claimed is:

1. A drilling needle (10), comprising:
a drilling needle head (1) arranged at one end of a drilling needle shank (2), the drilling needle head (1) comprising
    a flattened wedge portion (K) with two wedge faces (3), and
    a cutter portion(S) with two cutting faces (8),
    wherein the two cutting faces (8) each adjoin one of the two wedge faces (3), and
    wherein the two cutting faces (8) adjoin one another at a top edge (4) that runs at a right angle to an axis of rotation (A) of the drilling needle shank (2),
    wherein a respective relief face (7) laterally adjoins each of the two cutting faces (8),
    wherein each respective relief face (7)
        forms a cutting edge (5) with one of the two cutting faces (8) that leads with respect to a direction of rotation (r) and that extends from a top corner (4.1) at the top edge (4) to a cutting edge corner (5.1) at the wedge face (3), and
        forms a secondary edge (6) with another of the two cutting faces (8) that trails with respect to the direction of rotation (r) and that extends from the top corner (4.1) at the top edge (4) to a secondary edge corner (6.1) on the wedge face (3),
    wherein a relief angle (α), which a virtual straight line (h) that runs through the cutting edge corner (5.1) and the secondary edge corner (6.1) spans with a plane (E2) that extends perpendicular to the top edge (4) and includes the axis of rotation (A), lies in a range from 6° to 10°.

2. The drilling needle (10) according to claim 1,
wherein a cutting edge angle (γ) spanned by the cutting edge (5) with respect to the axis of rotation (a) lies in a range from 25° to 35°.

3. The drilling needle (10) according to claim 1,
wherein the top edge (4) provides a first diameter of rotation which is wider than a diameter of the drilling needle shank (2), wherein the drilling needle head (1), in a transition region of the wedge portion (K) with the cutter portion(S), has a second diameter of rotation that is larger than the first diameter of rotation, and
wherein an angle (δ) between the two wedge faces (3) is smaller than a top edge angle (β) between the two cutting faces (8).

4. The drilling needle (10) according to claim 3,
wherein the top edge angle (β) lies in a range from 85° to 95°.

5. The drilling needle (10) according to claim 1,
wherein the relief angle (α) is 8°.

6. The drilling needle (10) according to claim 1,
wherein the drilling needle (10) is made of steel and
wherein the drilling needle head (1) has a surface coating.

7. The drilling needle (10) according to claim 6,
wherein the surface coating is a hard chrome plating with a layer thickness in a range of 8 to 12 μm.

8. The drilling needle (10) according to claim 1,
wherein a width of the top edge (4) lies in a range of 2.00 to 2.50 mm; and
wherein a width of the drilling needle head (1) in a transition region of the wedge portion (K) with the cutter portion(S) lies in a range of 2.25 to 3.00 mm; and
wherein a height of the cutter portion (S) lies in a range of 0.30 to 0.40 mm.

9. A drilling resistance measuring device (12), comprising:
the drilling needle (10) according to claim 1; and
a hand-held device (11) including
    a drive device with a drill chuck in which the drilling needle (10) is clamped,
    a guide device for guided insertion of the drilling needle (10) into a wooden object (O) to be examined, and
    a drilling resistance detection device.

10. A method for examining properties of a wooden object (O), comprising:
providing the drilling resistance measuring device (12) according to claim 9;
inserting the drilling needle (10) into the wooden object (O) in an axial feed direction (e), which is arbitrary with respect to an object axis (H); and
creating a straight-line drilling channel in the axial feed direction (e).

\* \* \* \* \*